(12) United States Patent
Huang et al.

(10) Patent No.: US 12,329,915 B2
(45) Date of Patent: Jun. 17, 2025

(54) PULMONARY ARTERY STENT

(71) Applicant: SHANGHAI TENDFO MEDICAL TECHNOLOGIES CO., LTD., Shanghai (CN)

(72) Inventors: Dingguo Huang, Shanghai (CN); Huan Xia, Shanghai (CN)

(73) Assignee: SHANGHAI TENDFO MEDICAL TECHNOLOGIES CO., LTD., Shanghai (CN)

( * ) Notice: Subject to any disclaimer, the term of this patent is extended or adjusted under 35 U.S.C. 154(b) by 0 days.

(21) Appl. No.: 18/424,717

(22) Filed: Jan. 26, 2024

(65) Prior Publication Data

US 2024/0207035 A1    Jun. 27, 2024

Related U.S. Application Data

(63) Continuation of application No. 18/299,182, filed on Apr. 12, 2023, now Pat. No. 11,925,544, which is a
(Continued)

(30) Foreign Application Priority Data

Oct. 13, 2020   (CN) .......................... 202011089653.3
Oct. 13, 2020   (CN) .......................... 202022267001.6
(Continued)

(51) Int. Cl.
*A61M 25/00*   (2006.01)
*A61B 17/221*  (2006.01)
(Continued)

(52) U.S. Cl.
CPC ....... *A61M 25/0074* (2013.01); *A61B 17/221* (2013.01); *A61F 2/07* (2013.01);
(Continued)

(58) Field of Classification Search
None
See application file for complete search history.

(56) References Cited

U.S. PATENT DOCUMENTS

2003/0120263 A1   6/2003   Ouriel et al.
2004/0006370 A1   1/2004   Tsugita
(Continued)

FOREIGN PATENT DOCUMENTS

CN   101152111 A   4/2008
CN   202875544 U   4/2013
(Continued)

OTHER PUBLICATIONS

International Search Report in PCT/CN2020/142278 mailed on Sep. 16, 2021, 8 pages.
(Continued)

*Primary Examiner* — Rebecca S Preston
(74) *Attorney, Agent, or Firm* — Runzhi Lai

(57) ABSTRACT

The present disclosure provides a pulmonary artery stent. The pulmonary artery stent includes: a metal stent capable of circumferential expansion; and an isolation membrane wrapping the metal stent to isolate the metal stent from an external environment, and the isolation membrane having a circumferential tensile strength less than an axial tensile strength. The embodiments of the present disclosure can not only expand the diameter of the stent according to a change in the diameter of a blood vessel to meet a support performance requirement after the blood vessel enlarges but also isolate the metal portion of the stent from a vascular environment, thus effectively solving a problem of in-stent restenosis.

19 Claims, 20 Drawing Sheets

Related U.S. Application Data continuation-in-part of application No. PCT/CN2020/142279, filed on Dec. 31, 2020, and a continuation-in-part of application No. PCT/CN2020/142278, filed on Dec. 31, 2020.

(30) Foreign Application Priority Data

| Dec. 22, 2020 | (CN) | .......................... 202011529587.7 |
| Dec. 22, 2020 | (CN) | .......................... 202023115274.5 |

(51) Int. Cl.

| A61F 2/07 | (2013.01) |
| A61F 2/915 | (2013.01) |
| A61B 17/00 | (2006.01) |
| A61B 17/12 | (2006.01) |
| A61F 2/01 | (2006.01) |
| A61F 2/82 | (2013.01) |
| A61F 2/844 | (2013.01) |
| A61F 2/848 | (2013.01) |
| A61F 2/89 | (2013.01) |

(52) U.S. Cl.

CPC ........ *A61F 2/915* (2013.01); *A61B 17/00234* (2013.01); *A61B 17/12113* (2013.01); *A61F 2/01* (2013.01); *A61F 2002/016* (2013.01); *A61F 2002/072* (2013.01); *A61F 2002/828* (2013.01); *A61F 2/844* (2013.01); *A61F 2002/8483* (2013.01); *A61F 2/89* (2013.01); *A61F 2220/0016* (2013.01); *A61F 2250/0003* (2013.01); *A61F 2250/0068* (2013.01); *A61M 2025/0008* (2013.01); *A61M 25/003* (2013.01); *A61M 2025/0057* (2013.01)

(56) References Cited

U.S. PATENT DOCUMENTS

| 2007/0208409 A1 | 9/2007 | Quigley |
| 2008/0188925 A1 | 8/2008 | Zhao |
| 2010/0016832 A1* | 1/2010 | Thai .................... A61M 25/003 604/528 |
| 2016/0166801 A1 | 6/2016 | Birdsall et al. |
| 2019/0133618 A1* | 5/2019 | Green .................. A61B 17/221 |
| 2020/0085561 A1 | 3/2020 | Derkvist |
| 2022/0117718 A1 | 4/2022 | Yi et al. |

FOREIGN PATENT DOCUMENTS

| CN | 103284775 A | 9/2013 |
| CN | 205411914 U | 8/2016 |
| CN | 205434012 U | 8/2016 |
| CN | 208838262 U | 5/2019 |
| CN | 112120759 A | 12/2020 |
| CN | 112535561 A | 3/2021 |
| CN | 113101024 A | 7/2021 |
| WO | 2007095233 A2 | 8/2007 |

OTHER PUBLICATIONS

Written Opinion in PCT/CN2020/142278 mailed on Sep. 16, 2021, 7 pages.
International Search Report in PCT/CN2020/142279 mailed on Jun. 24, 2021, 9 pages.
Written Opinion in PCT/CN2020/142279 mailed on Jun. 24, 2021, 9 pages.

* cited by examiner

PULMONARY ARTERY STENT

CROSS-REFERENCE TO RELATED APPLICATIONS

This application is a continuation of U.S. patent application Ser. No. 18/299,182, filed on Apr. 12, 2023, which is a continuation-in-part application of International Patent Application No. PCT/CN2020/142278, filed on Dec. 31, 2020, which claims priority to Chinese Patent Application No. 202011529587.7, filed on Dec. 22, 2020, and claims priority to Chinese Patent Application No. 202023115274.5, filed on Dec. 22, 2020. The U.S. patent application Ser. No. 18/299,182 is also a continuation-in-part application of International Patent Application No. PCT/CN2020/142279, filed on Dec. 31, 2020, which claims priority to Chinese Patent Application No. 202011089653.3, filed on Oct. 13, 2020, and claims priority to Chinese Patent Application No. 202022267001.6, filed on Oct. 13, 2020. The contents of each of the above-related applications are hereby incorporated by reference.

TECHNICAL FIELD

The present disclosure relates to the technical field of a medical device, and in particular, to a pulmonary artery stent.

BACKGROUND

Pulmonary artery stenosis is comparatively common in complex congenital heart disease, along with the development of percutaneous interventional treatment technology, inserting an implant for treating pulmonary artery stenosis has become an effective treatment mean for pulmonary artery stenosis. The application of the implant for treating pulmonary artery stenosis in interventional surgery has shown good results in pulmonary artery stenosis, right ventricular outflow tract stenosis, channel stenosis after corrective complex congenital heart disease, and systemic pulmonary shunt conduit and collateral blood vessel stenosis. The specific interventional surgery includes introducing a special guide wire, catheter, and the implant for treating pulmonary artery stenosis in the human body under the guidance of a medical imaging device and performing surgical treatment on the pulmonary artery stenosis in the human body. The interventional treatment of the implant for pulmonary artery stenosis has the characteristics of less trauma, quick recovery, and good effect.

Pulmonary artery stenosis caused by congenital heart disease mainly occurs in a 10-20 years old crowd. The body of this crowd is in a growth and development stage, and the blood vessel size may increase with age. However, a traditional vascular stent cannot meet the changes in the blood vessel size over time; secondly, the local irritation of the pulmonary artery by the implantation of the traditional vascular stent will further lead to intimal hyperplasia, resulting in a problem of in-stent restenosis. Furthermore, due to the physiological structure of the pulmonary artery being located at the right ventricular outflow, when the heart contracts and pumps blood out of the ventricle into the pulmonary artery, the blood flow velocity and blood pressure are relatively high. After the traditional vascular stent is implanted, it is easy to be displaced under the impact of the blood flow, resulting in failure.

Meanwhile, in addition to congenital heart disease, another common cause of abnormalities in the pulmonary artery-related cardiovascular system is pulmonary embolism. Pulmonary embolism is often caused by deep vein thrombosis in the lower extremities and has a high mortality rate, which seriously endangers the health and quality of life of patients. Existing manners for the treatment of pulmonary embolism mainly include drug anticoagulation, thrombolysis, traditional surgery, and interventional treatment. However, the traditional catheter thrombolysis process needs to place the thrombolysis catheter in the body for a long time and needs to use a large dose of a thrombolysis agent, which causes that the thrombolysis efficiency is low and a large amount of the thrombolysis agent is wasted. Therefore, there is an urgent need to develop a drug injection stent that can effectively deliver drugs to a target site.

SUMMARY

One or more embodiments of the present disclosure provide a pulmonary artery stent. The pulmonary artery stent may not only be expanded as a diameter of a blood vessel increases to make the stent continuously provide sufficient support to the blood vessel but also isolate a metal portion of the stent from a vascular environment, thereby effectively solving a problem of in-stent restenosis.

One or more embodiments of the present disclosure provide a pulmonary artery stent including: a metal stent capable of circumferential expansion; and an isolation membrane wrapping the metal stent to isolate the metal stent from an external environment, and the isolation membrane having a circumferential tensile strength less than an axial tensile strength.

One or more embodiments of the present disclosure provide a metal stent capable of circumferential expansion as a support structure, so that the metal stent may be expanded when a diameter of a patient's blood vessel varies widely to continuously ensure the support of the stent to the blood vessel. At the same time, the metal stent is isolated from a vascular environment by wrapping the metal stent with an isolation membrane to prevent the metal stent from irritating the blood vessel and causing intimal hyperplasia, which can effectively prevent the in-stent restenosis.

In some embodiments, the metal stent includes: a plurality of support segments; the isolation membrane includes an inner film and a plurality of segments of a strip-shaped or cylinder-shaped outer film; the inner film covers an inner surface of the metal stent, and each segment of the outer film is connected to the inner film and covers each of the support segments, respectively; and the each of the support segments is connected by the isolation membrane.

In some embodiments, at least one segment of the outer film has a skirt, and a drug storage slot is formed between the skirt and the inner film.

In some embodiments, the isolation membrane is a polytetrafluoroethylene film and forms a smooth blood flow channel surface after wrapping the metal stent.

In some embodiments, the support segments include a plurality of end-to-end support ribs arranged in a wavy shape, and the support segments are formed by surrounding the support ribs along an arrangement direction; the support segments include a plurality of common ribs and elongated ribs; and the each of the support segments has a plurality of common ribs with a telescopic segment, and a plurality of telescopic segments in a same support segment are evenly distributed in a circumferential direction.

In some embodiments, portions of support ribs of adjacent support segments axially overlap.

In some embodiments, the support segments include a plurality of double wave segments arranged in a circumferential direction, the double wave segments include two wave segments, and the two segments are symmetrically arranged; wherein each of the two wave segments is composed of a plurality of end-to end support ribs arranged in a wavy shape, support ribs located at connecting ends of the double wave segments and in close proximity to each other are used as connecting ribs, and connecting ribs of any two double wave segments adjacent to each other in the circumferential direction are cross-connected.

In some embodiments, all double wave segments arranged in the circumferential direction in the each of the support segments are connected to form a single layer double wave support unit, and the each of the support segments further includes a reinforcing layer double wave support unit; and an arrangement structure of support ribs of the reinforcing layer double wave support unit is similar to an arrangement structure of support ribs of the single layer double wave support unit, vertices are formed at joints of the support ribs of the reinforcing layer double wave support unit, and vertices on axial sides of the reinforcing layer double wave support unit are integrally connected to vertices of corresponding positions of the single layer double wave support unit.

In some embodiments, a connecting rib of the two wave segments has a telescopic segment.

In some embodiments, a double-bending bridging structure is used between the two wave segments to achieve that the connecting ribs of any two double wave segments adjacent to each other in the circumferential direction are cross-connected.

In some embodiments, the telescopic segment includes a plurality of end-to-end metal wires arranged in a wavy shape.

In some embodiments, the metal stent is provided with a plurality of barbs distributed in a circumference direction.

In some embodiments, the pulmonary artery stent and a drug injection thrombolysis system may constitute a pulmonary artery vascular treatment device. The drug injection thrombolysis system includes a delivery assembly, an external drug injection assembly, and a drug injection stent. The drug delivery assembly includes a sheath tube and a delivery handle, and the sheath tube is fixedly connected to the delivery handle. The drug injection stent is stored at an inner end of the sheath tube. The drug injection stent includes: a drug delivery tube, a stent body capable of radial elastic expansian, and a thrombus filler. The stent body is fixed on the drug delivery tube and includes a plurality of elastic tubes forming a stent structure. The elastic tubes are connected to the drug delivery tube and provided with a plurality of drug injection holes. The thrombus filler is fixed on the drug delivery tube and is located at a distal end of the stent body. The external drug injection assembly includes a drug injection connector and a syringe. The drug delivery tube of the drug injection stent is penetrated into the drug delivery assembly, an outer end of the drug delivery tube is connected to the drug injection connector, and the drug injection connector is connected to the syringe.

One or more embodiments of the present disclosure also provide a drug injection stent and a drug injection thrombolysis system containing the drug injection stent. By releasing a drug injection stent capable of elastic expansion at a position of a thrombus, a thrombolysis agent is injected after the drug injection stent is embedded in the thrombus, thereby allowing the thrombolysis agent to act directly and precisely on the thrombus in a large area, improving the efficiency of thrombolysis, and facilitating saving of the thrombolysis agent and a treatment time.

One or more embodiments of the present disclosure also provide a drug injection stent including: a drug delivery tube, a stent body capable of radial elastic expansion, and a thrombus filter. The stent body is fixed on the drug delivery tube, and includes a plurality of elastic tubes forming a stent structure. The elastic tubes are connected to the drug delivery tube and are provided with a plurality of drug injection holes. The thrombus filter is fixed to the drug delivery tube and is located at a distal end of the stent body.

Embodiments of the present disclosure also provide a drug injection thrombolysis system including: a delivery assembly, an external drug injection assembly, and a drug injection stent as previously described. The drug delivery assembly includes a sheath tube and a delivery handle. The sheath tube is fixedly connected to the delivery handle. The drug injection stent is stored at an inner end of the sheath tube. The external drug injection assembly includes a drug injection connector and a syringe. The drug delivery tube of the drug injection stent is penetrated within the drug delivery assembly, an outer end of the drug delivery tube is connected to the drug injection connector, and the drug injection connector is connected to the syringe.

Embodiments of the present disclosure provide a drug injection stent and a drug injection thrombolysis system containing the drug injection stent, the drug injection stent includes a stent body fixed on a drug delivery tube, the stent body includes a plurality of elastic tubes forming a stent structure. The elastic tubes are connected to the drug delivery tube and are provided with a plurality of drug injection holes. The drug injection thrombolysis system includes a delivery assembly and an external drug injection assembly, and the delivery assembly includes a sheath tube for storing the drug injection stent and a delivery handle connected to the sheath tube. The external drug injection assembly includes a drug injection connector and a syringe, the drug delivery tube is penetrated into the delivery assembly and connected to the drug injection connector, and the drug injection connector is connected to the syringe. Therefore, this embodiment may load the drug injection stent in the sheath tube, transport the drug injection stent to the position of the thrombus by the delivery handle, and then retract the sheath tube by the delivery handle, so that the drug injection stent may be embedded in the thrombus after it expands itself at the position of the thrombus, and then inject the thrombolysis agent into the drug injection stent by the syringe, so that the thrombolysis agent can be precisely sprayed on the thrombus through the drug injection stent, thus making the thrombolysis agent act on the thrombus in a large area, which allows the thrombolysis agent to act on the thrombus in a large area, thereby improving the efficiency of thrombolysis and saving the amount of the thrombolysis agent and the treatment time.

In some embodiments, the stent body is a stent unit; and at least one end of each elastic tube of the stent body is connected to the drug delivery tube; or the stent body includes a plurality of stent units, and the plurality of stent units are arranged axially aligned or staggered along the drug delivery tube.

In some embodiments, the drug injection holes are evenly distributed on the elastic tubes; and wherein drug injection holes at each open position are single holes or double holes symmetrically distributed.

In some embodiments, the drug delivery tube is provided with a side hole at a position of the stent body.

In some embodiments, the drug delivery tube is provided with a developing part for indicating the position of the stent body at the position of the stent body.

In some embodiments, the elastic tubes extend spirally in an axial direction of the drug delivery tube.

In some embodiments, the stent body is made of an elastic metal tube or an elastic polymer material tube.

In some embodiments, the sheath tube is threadedly connected to the delivery handle, and the sheath tube is a sheath tube capable of elastic retraction; and the sheath tube has a caliber larger than a diameter of an inlet of the delivery handle when naturally opened.

In some embodiments, the system further includes a recovery handle. The recovery handle is slidingly connected to the delivery handle, the recovery handle is fixedly connected to the drug injection connector, and the drug delivery tube is penetrated into the recovery handle.

BRIEF DESCRIPTION OF THE DRAWING

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, wherein.

DETAILED DESCRIPTION

Figure 1:
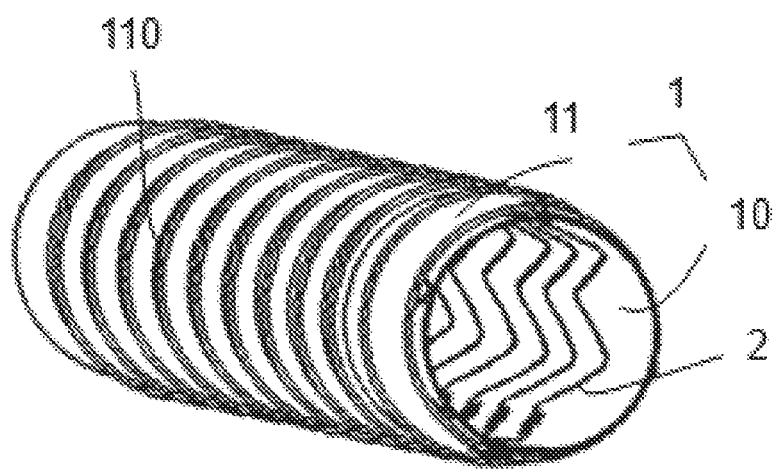
FIG. 1 is a schematic diagram illustrating a three-dimensional structure of a pulmonary artery stent according to some embodiments of the present disclosure.
Figure 2:
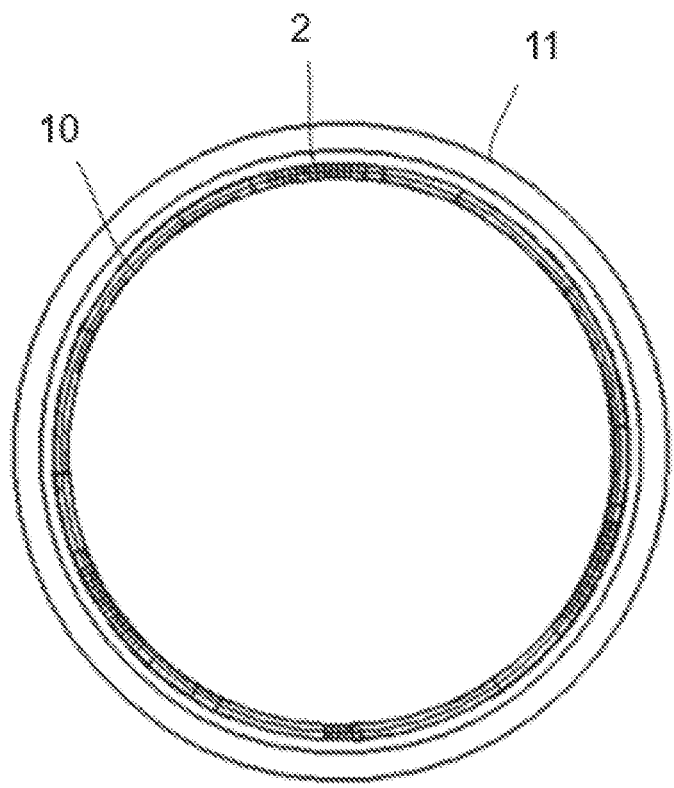
FIG. 2 is a schematic diagram illustrating a cross-sectional structure of the pulmonary artery stent according to some embodiments of the present disclosure.

The technical solutions of embodiments of the present disclosure will be more clearly described below, and the accompanying drawings need to be configured in the description of the embodiments will be briefly described below. Obviously, drawings described below are only some examples or embodiments of the present disclosure. Those skilled in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system", "device", "unit", and/or "module" used herein are one method to distinguish different components, elements, parts, sections, or assemblies of different levels in ascending order. However, the terms may be displaced by other expressions if they may achieve the same purpose.

As shown in the present disclosure and claims, unless the context clearly prompts the exception, "a", "one", and/or "the" is not specifically singular, and the plural may be included. It will be further understood that the terms "comprise," "comprises," and/or "comprising," "include," "includes," and/or "including," when used in the present disclosure, specify the presence of stated steps and elements, but do not preclude the presence or addition of one or more other steps and elements thereof.

The flowcharts are used in present disclosure to illustrate the operations performed by the system according to the embodiment of the present disclosure. It should be understood that the front or rear operation is not necessarily performed in order to accurately. Instead, the operations may be processed in reverse order or simultaneously. Moreover, one or more other operations may be added to the flowcharts. One or more operations may be removed from the flowcharts.

A first embodiment of the present disclosure provides a pulmonary artery stent suitable for endovascular interventional treatment of pulmonary artery stenosis. As shown in FIGS. 1-7, the pulmonary artery stent includes: a metal stent 2 capable of circumferential expansion, an isolation membrane 1 wrapping the metal stent 2 to isolate the metal stent 2 from an external environment, and a circumferential tensile strength of the isolation membrane 1 is less than an axial tensile strength.

In some embodiments, the isolation membrane 1 may be a polytetrafluoroethylene film, and a circumferential tensile strength of the polytetrafluoroethylene film is less than the axial tensile strength, i.e., when the metal stent 2 expands circumferentially, the isolation membrane 1 wrapping it also expands, but an axial size of the isolation membrane 1 is not easily increased, so that a length of the metal stent may be kept substantially constant.

In some embodiments, the metal stent 2 wrapped by the isolation membrane 1 may be a reticulated tubular body as a whole, and its tube diameter may be variable or the same everywhere, which is not specifically limited here. The metal stent 2 may be obtained by processing a medical metal pipe (such as stainless steel or cobalt-based alloy) that may deform under force but has a certain strength through laser cutting and electrochemical polishing. In some embodiments, the metal stent 2 may also be obtained by other processing processes, which is not specifically limited here. For more information about the metal stent, please refer to other parts of the present disclosure, such as the descriptions of FIG. 3, FIG. 4, FIG. 13, and other parts.

The pulmonary artery stent of this embodiment uses the metal stent capable of circumferential expansion as a vascular support structure so that the metal stent may be expanded when a diameter of a patient's blood vessel increases to continuously ensure the support of the stent to the blood vessel. The metal stent is isolated from the vascular environment by being wrapped by the isolation membrane to prevent the metal stent from irritating the blood vessel and causing intimal hyperplasia, which can effectively prevent the problem of in-stent restenosis.

Figure 3:
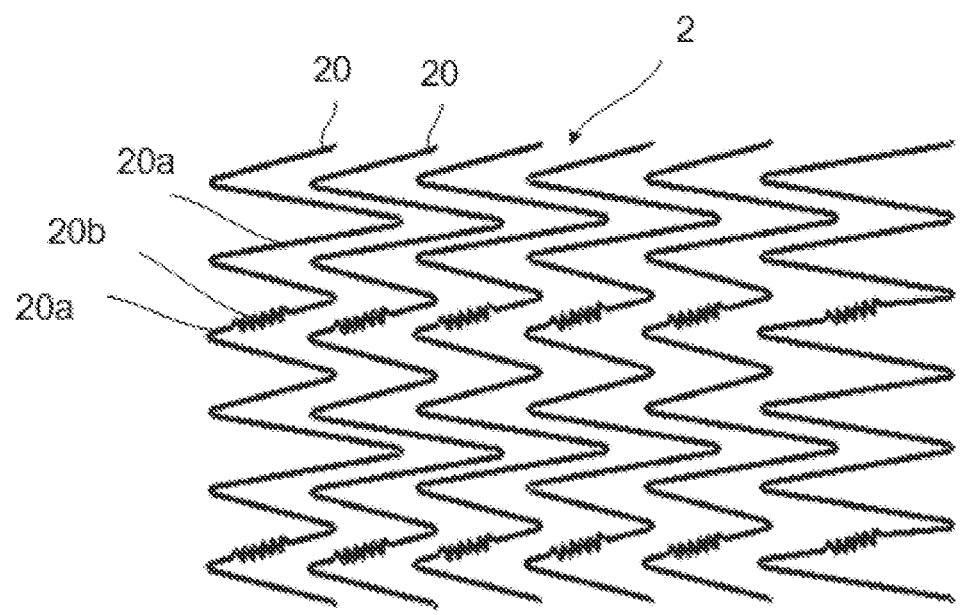
FIG. 3 is a schematic diagram illustrating an exemplary structure of a metal stent of the pulmonary artery stent according to some embodiments of the present disclosure.

FIG. 3 shows an exemplary expanded structure of the metal stent 2. As shown in FIG. 3, the metal stent 2 may include a plurality of support segments 20, and each of the support segments 20 is arranged axially. The metal stent shown in FIG. 3 includes six support segments 20 arranged coaxially. In some embodiments, the metal stent may include a greater or lesser number of support segments 20.

In some examples, the metal stent 2 may also be one individual support segment. The each of the support segments 20 includes a plurality of end-to end support ribs 20a arranged in a wavy shape and is formed by surrounding the support ribs in an arrangement direction, i.e., the plurality of support ribs are arranged end to end to form a reticulated columnar surface, which constitutes a support structure capable of circumferential expansion, the circumferential expansion of which is realized by the deformation of the support ribs arranged in the wavy shape in the each of the support segments, and the deformation of the support ribs arranged in the wavy shape is not structurally limited and has a large radial expansion range. In some processes of use, the diameter of the metal stent 2 after a re-expansion may reach twice the diameter after a first expansion. Thus, the metal stent may be expanded according to a size of an enlarged blood vessel to cause the metal stent to provide suitable support to a stenosis blood vessel.

In this embodiment, each of the support segments 20 includes a plurality of common ribs and elongated ribs, the common ribs and elongated ribs are both support ribs, and a difference is that the lengths of the common ribs and elongated ribs are different. The widths or other sizes of the common ribs and elongated ribs may also be different. Preferably, each of the support segments 20 has a plurality of common ribs with a telescopic segment 20b, and a plurality of telescopic segments 20b in a same support segment 20 are evenly distributed in a circumferential direction.

As shown in FIG. 3, the telescopic segment 20b may be composed of a plurality of metal wires that are connected end to end and arranged in a wavy shape, i.e., an axial extension structure of the telescopic segment is similar to a circumferential expansion structure of the support segment. The each of the support segments 20 may include 2m elongated ribs and 2n common ribs, wherein m and n are positive integers greater than or equal to 1, respectively. A length of each elongated rib is substantially the same, a length of each common rib is substantially the same, and a long bending structure formed by connecting every 2 elongated ribs is staggered with a short bending structure formed by connecting every 2 common ribs.

In some embodiments, each of the support segments 20 shown in FIG. 3 may be composed of 4 elongated ribs and 8 common ribs, respectively. The 4 elongated ribs constitute 2 long bending structures and the 8 common ribs constitute 4 short bending structures. The 2 long bending structures and the 4 short bending structures are staggered in the circumferential direction. 2 telescopic segments are disposed on 2 common ribs evenly staggered in the circumferential direction, respectively, so that the telescopic segments 20b in the each of the support segments 20 are evenly arranged in the circumferential direction.

The elongated ribs in the support segments 20 help to increase a circumferential expansion range of the metal stent, and the telescopic segments 20b therein may avoid an axial retraction of the metal stent as much as possible while increasing the circumferential expansion range of the metal stent. As shown in FIG. 3, crests of the support structure arranged in a wavy shape of each of the support segments 20 are axially aligned, and the telescopic segments 20b are also axially aligned.

In some embodiments, portions of the support ribs 20a of adjacent support segments 20 may axially overlap, resulting in better support performance of the metal stent 2. In some embodiments, the support ribs 20a of the support segments 20 may also not axially overlap. In this embodiment, each of the support segments 20 is a repeating unit with the same structure, but is not limited to this. In other examples, the structure of each of the support segments may also be different. In this embodiment, there is no specific limitation on the number, length, arrangement of the support ribs, and the structure of the telescopic segments in the support segments.

Figure 4:
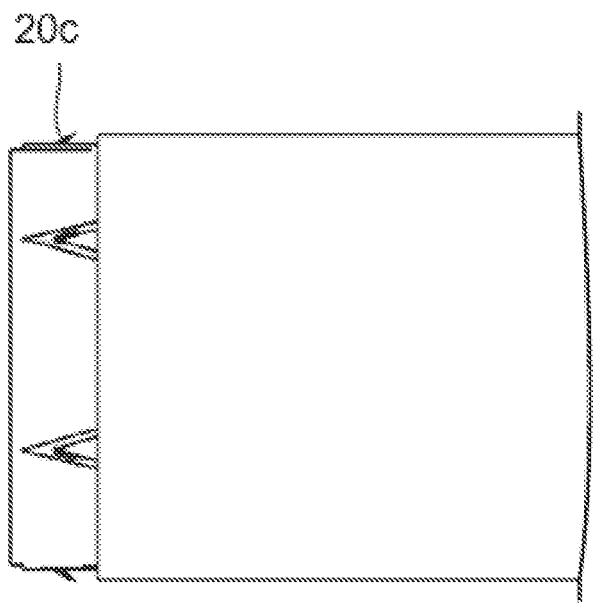
FIG. 4 is a schematic diagram illustrating an exemplary structure of a barb of the pulmonary artery stent according to some embodiments of the present disclosure.

As shown in FIG. 4, the metal stent 2 may also be provided with a plurality of barbs 20c distributed in the circumferential direction. In some embodiments, the plurality of barbs 20c may be provided at a plurality of vertex positions of a first support segment of the metal stent 2 in the circumferential direction, and the first support segment corresponds to a blood inflow end. When the pulmonary artery stent is placed in the patient's pulmonary artery vessel, the barbs 20c may be pierced into the vessel wall to anchor the pulmonary artery stent in the blood vessel, which reduces a risk of stent displacement when the blood flow velocity is high or the blood pressure is high.

Figure 5:
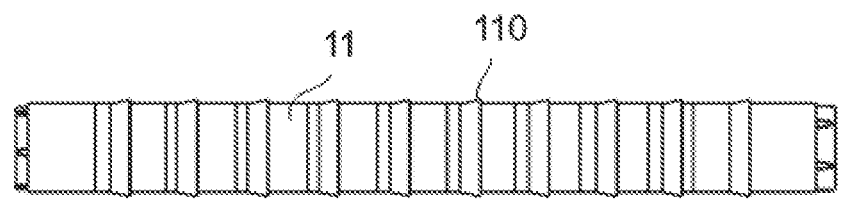
FIG. 5 is a schematic diagram illustrating an exemplary structure of the pulmonary artery stent according to some embodiments of the present disclosure.

As shown in FIGS. 1 and 5, the isolation membrane 1 includes an inner film 10 and a plurality of segments of a strip-shaped or cylinder-shaped outer film 11. The inner film 10 covers an inner surface of the metal stent 2, and each segment of the outer film 11 is connected to the inner film 10 and covers each of the support segments 20, and the each of the support segments 20 is connected by the isolation membrane 1.

In some embodiments, a surface of the isolation membrane is coated with a surface coating containing a biological drug. The surface coating refers to a coating formed by a biological drug and is capable of being coated on the surface of the outer film. In some embodiments, the biological drug coated on the surface of the outer film may include at least one of growth factor, BMP-2, thrombin, and insulin. Since the outer film over the pulmonary artery stent is in direct contact with the pulmonary artery vessels for a long time, it may cause problems such as thrombosis, infection, and cell proliferation. The biological drug coated on the surface coating of the pulmonary artery may be a relevant biological drug that inhibits the cell proliferation, prevents the infection, reduces the thrombosis, etc., thereby reducing sequelae arising from the pulmonary artery stent being placed in the blood vessels for a long time.

In some embodiments, the isolation membrane may be a membrane formed using a synthetic or natural polyelectrolyte material, and the outer film may adsorb biological drugs from solutions containing different biological drug components by initially complementary interactions (e.g., polycation-polyanion, donor-acceptor hydrogen bonding interactions), respectively, and sequentially deposit the different biological drugs layer by layer on the surface of the outer film. Surface properties of the outer film may change with a process of adsorbing different biological drugs from solutions containing different biological drug components. By repeating the process several times, a surface coating with an appropriate biological drug and coating thickness may be obtained, and different biological drugs are sequentially deposited and fixed on the outer film.

In some embodiments, the synthetic or natural polyelectrolyte material may be various, for example, the polyelectrolyte material may be a hydrogen bond donor polyacrylic acid, chitosan, polysaccharide hyaluronic acid, polyalginic acid, etc. In some embodiments, the biological drug is coated on the surface of the outer film in a hydrophilic mode to form the surface coating, which can avoid destroying certain biological drugs that are unstable in properties.

In some embodiments, the isolation membrane coated with a multilayer biological drug coating is highly hydrophilic due to using a polyelectrolyte material, which may be used to control cell adhesion and proliferation in blood vessels by controlling mechanical properties (e.g., elasticity) of the isolation membrane.

In some embodiments, the multilayer biological drug coating may have other effects, such as controlling a "depth" of a position of the biological drug by controlling the formation of the coating, or even controlling a distribution of two or more drugs in different positions, thereby achieving a function of releasing a specific biological drug at a specific time point. For example, if the outer film needs to form a surface coating containing two biological drugs A and B, and A needs to be released earlier than B, then B may be adsorbed and deposited from a solution containing B, and A may be adsorbed from a solution containing A and deposited on B.

In some embodiments, the support segments of the metal stent 2 are maintained as an integral stent structure directly through the isolation membrane, thereby allowing the elimination of a connecting structure between the support segments. Specifically, the inner film 10 may be a film layer whose length and diameter are adapted to the length and diameter of the metal stent 2, i.e., the inner film 10 may wrap an entire inner surface of the metal stent 2 when each of the support segments 20 of the metal stent 2 is placed on an outer surface of the inner film 10.

In actual applications, the inner film may be placed on a tubular mold, the each of the support segments of the metal stent may be sequentially placed on the outer surface of the inner film, and then each segment of the cylinder shaped outer film 11 may be individually placed on a corresponding support segment, or each segment of the strip shaped outer film 11 may be wrapped around a corresponding support segment. Each segment of the outer film is hot-fused or bonded to the inner film so that the each support segment is wrapped in the film layer. In this embodiment, the isolation membrane 1 forms a smooth blood flow channel surface after wrapping the metal stent 2, i.e., the inner surface of the isolation membrane is smooth and wrinkle-free, so that the generation of the thrombus can be effectively prevented.

In some embodiments, vertices of the support segments 20 are formed at joints of the support ribs 20a of the support segments 20, and in order to ensure the circumferential expansion performance of each of the support segments 20, the vertices of the support segments 20 and the support ribs 20a may have a certain movable region within the isolation membrane 1. Therefore, a joint region (a hot-fused or bonded region) of the outer film 11 and the inner film 10 may be provided outside the vertices of the support segments 20 and the movable region of the support ribs.

Figure 6:
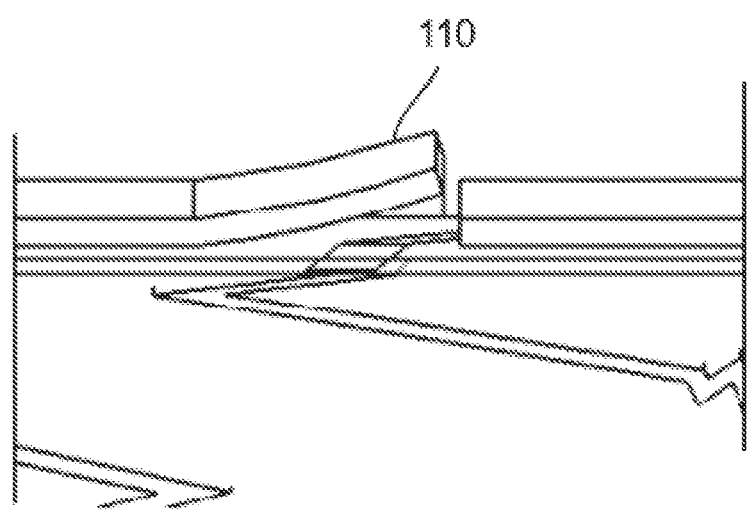
FIG. 6 is a schematic diagram illustrating a structure of a skirt of the pulmonary artery stent according to some embodiments of the present disclosure.
Figure 7:
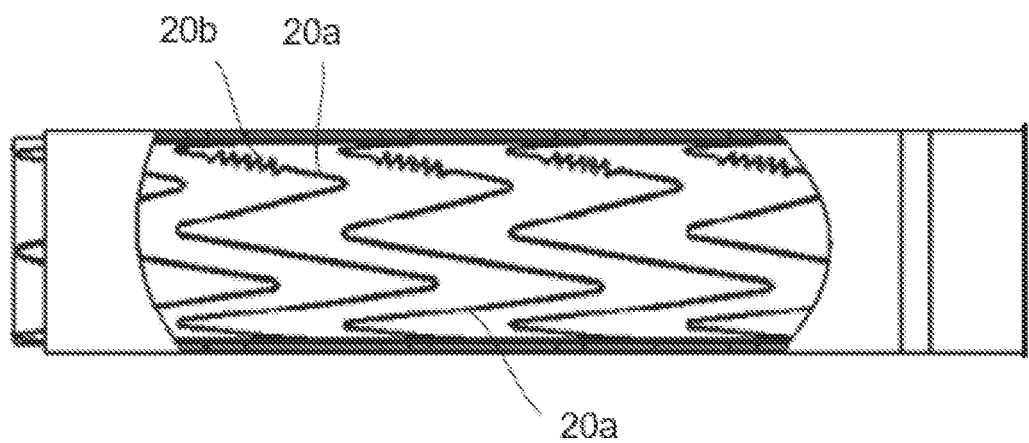
FIG. 7 is a schematic diagram illustrating a partially dissected structure of the pulmonary artery stent according to some embodiments of the present disclosure.

In some embodiments, at least one segment of the outer film 11 has a skirt 110, and a drug storage slot is formed between the skirt 110 and the inner film 10. The skirt is a film segment with a certain length retained on the outer film that is not connected to the inner film 10. Therefore, a pocket-like drug storage slot structure is formed between the skirt 110 and the inner film 10. As shown in FIGS. 1, 5, and 6, each segment of the outer film 11 has a skirt so that a drug storage slot is formed at the each segment of the outer film 11. The drug storage slot may be used to store anti-blood vessel stenosis drugs and used for targeted delivery of the drugs during treatment, and the barrier effect of the film may achieve a certain drug-sustained release effect.

The pulmonary artery stent of this embodiment may be expanded twice during use according to the patient's blood vessel growth, thereby providing sufficient support to the pulmonary artery on a continuous basis. The isolation membrane isolates the metal stent from the vascular environment, which effectively prevents the problem of in-stent restenosis, and the barbs enable to make the stent more reliably anchored on the vessel wall, which prevents the stent from shifting during use.

A second embodiment of the present disclosure provides a pulmonary artery stent. The main difference between this embodiment and the first embodiment is that the structure of the support segments of the metal stent in the second embodiment is different from that in the first embodiment.

Figure 8:
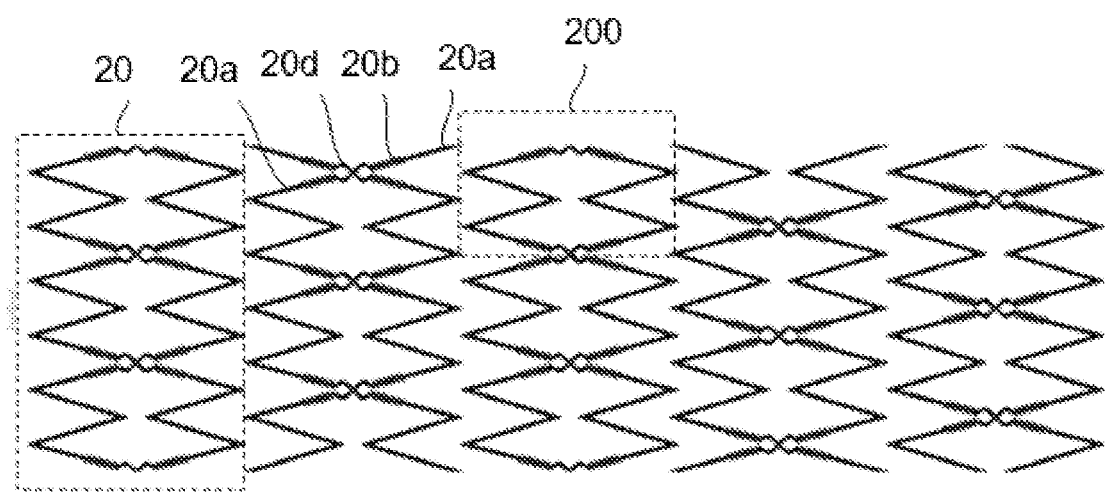
FIG. 8 is a schematic diagram illustrating the structure of the metal stent of the pulmonary artery stent according to some embodiments of the present disclosure.

As shown in FIG. 8, the support segments 20 of the metal stent 2 of the pulmonary artery stent include a plurality of double wave segments 200 arranged in a circumferential direction, the double wave segments 200 include two wave segments, and the two wave segments are symmetrically arranged. Each of the two wave segments is composed of a plurality of end-to-end support ribs 20a arranged in a wavy shape, and the support ribs 20a located at connecting ends of the double wave segments 200 and close to each other are used as connecting ribs, and connecting ribs of any two double wave segments adjacent to each other in the circumferential direction are cross-connected, so that each wave segment on the same side in an axial direction in the adjacent double wave segments is connected to form a single support unit in the circumferential direction. Two single support units are connected in the axial direction at the same time. In this embodiment, each support rib 20a in the two single support units in the support segments 20 has approximately the same length, which is conducive to maintaining a more balanced support force on the vessel wall in the circumferential direction for the stent after expansion compared with structures having elongated ribs and common ribs.

In some embodiments, the wave segments are cross-connected using a double-bending (i.e., "S" shaped) bridging structure 20d, thereby facilitating the avoidance of the axial retraction of the stent. Optionally, the support ribs 20a of each wave segment may have a telescopic segment 20b, where the telescopic segment 20b may be composed of a plurality of end-to-end metal wires arranged in a wave shape. The stent may have better expansion performance through the telescopic segment and the double-bending bridging structure.

As shown in FIG. 8, each support segment 20 may be a repeating unit with the same structure, and the crests of the support structures arranged in a wavy shape of adjacent support units in adjacent support segments 20 are axially aligned, though not limited to this, in other examples, the crests and valleys of adjacent support structures arranged in the wavy shape may also be axially aligned.

Figure 9:
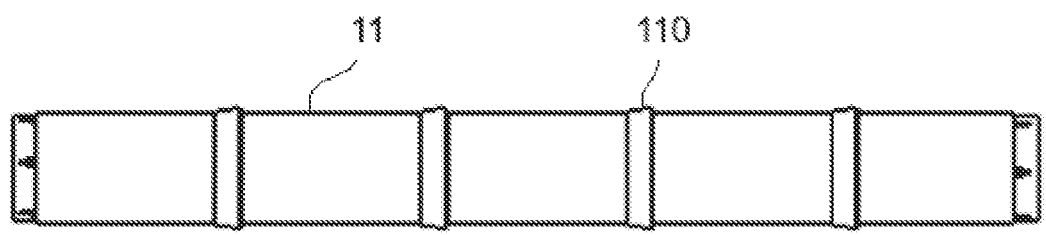
FIG. 9 is a schematic diagram illustrating the structure of the pulmonary artery stent according to some embodiments of the present disclosure.
Figure 10:
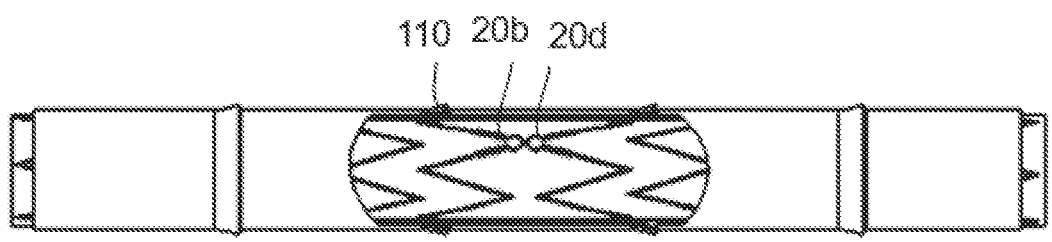
FIG. 10 is a schematic diagram illustrating the partially dissected structure of the pulmonary artery stent according to some embodiments of the present disclosure.
Figure 11:
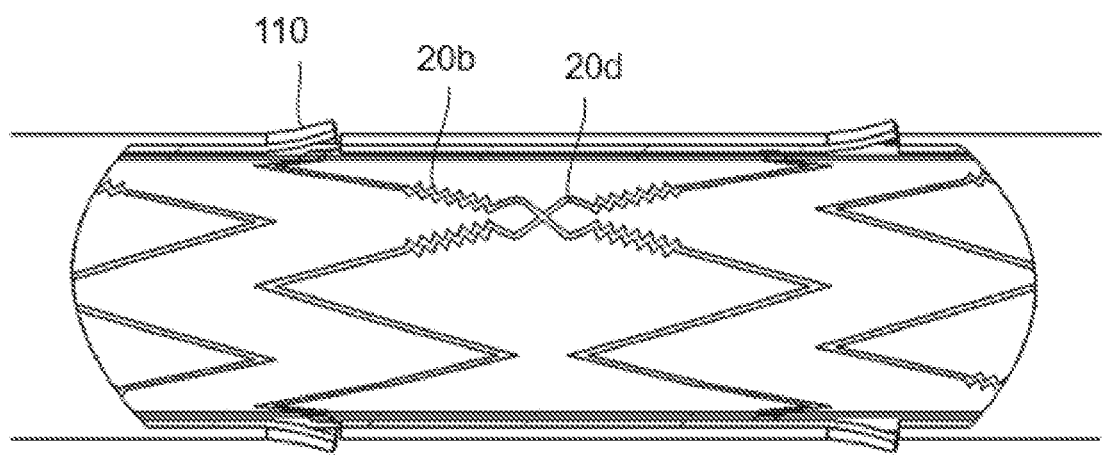
FIG. 11 is an enlarged schematic diagram illustrating the dissected portion shown in FIG. 10.

As shown in FIGS. 9-11, the plurality of support segments are wrapped by the inner film and the isolation membrane formed by the plurality of segments of the outer film 11. The relevant structure of the isolation membrane is similar to that of the first embodiment and is not repeated here.

For the pulmonary artery stent of this embodiment, not only the expansion performance is good and the axial retraction is not easy, but also the support force is more balanced.

A third embodiment of the present disclosure provides a pulmonary artery stent. This embodiment makes further improvements to the structure of the support segments of the metal stent based on the second embodiment.

Figure 12:
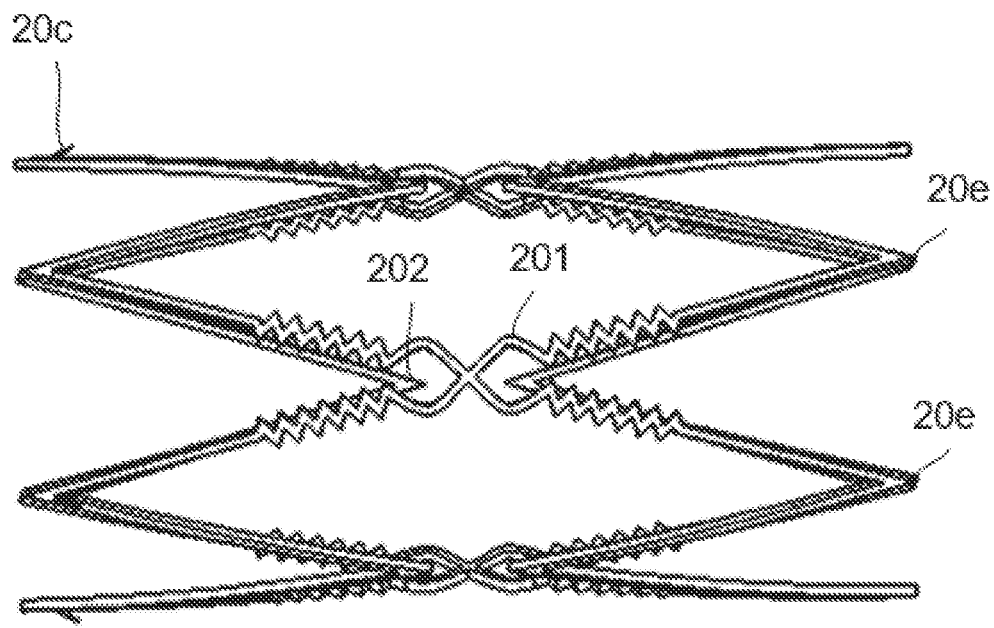
FIG. 12 is a schematic diagram illustrating a partial structure of the metal stent according to some embodiments of the present disclosure.

As shown in FIG. 12, the metal stent of the pulmonary artery stent of this embodiment includes two layers of support structures, and this embodiment does not specifically limit the number of layers of the support structures. The metal stent of the pulmonary artery stent includes a plurality of support segments 20, each support segment 20 includes a plurality of double wave segments as described in the second embodiment, all double wave segments arranged in the circumferential direction in the each of the support segments 20 are connected to form a single layer double wave support unit 201, and the each of the support segments also includes a reinforcing layer double wave support unit 202. An arrangement structure of support ribs of the enhanced layer double wave support unit is similar to an arrangement structure of support ribs of the single layer double wave support unit, vertices 20e are formed at joints of the support ribs 20a of the reinforcing layer double wave support unit, and vertices 20e on axial sides of the reinforcing layer double wave support unit are integrally connected to vertices 20e of corresponding positions of the single layer double wave support unit.

In this embodiment, the structure of the single layer double wave support unit 201 may be the same as the structure of the support segments of the second embodiment. The reinforcing layer double wave support unit 202 differs from the single layer double wave support unit 201 in that the reinforcing layer double wave support unit 202 is a double wave structure, but the double waves need not be connected to each other, and the vertices 20e on both axial sides of the reinforcing layer double wave support unit 202 are integrally connected to the vertices on both axial sides of the single layer double wave support unit 201, thereby making it possible to connect the reinforcing layer double wave support unit 202 and the single layer double wave support unit 201 into one.

The plurality of support segments in the metal stent of the pulmonary artery stent of this embodiment are similarly wrapped by an inner film and an isolation membrane formed by a plurality of segments of an outer film, and the structure of the isolation membrane is similar to that of the preceding embodiment, which is not repeated herein.

The pulmonary artery stent of this embodiment has better structural strength to meet the requirements of greater blood vessel support strength.

In conjunction with FIG. 1, manners and steps for using the pulmonary artery stent of this embodiment are as follows.

A device interventional channel is established in a femoral vein vessel by means of a puncture needle, guide wire, catheter, and small puncture sheath. The catheter is introduced via an intravascular interventional channel technique to blood vessel stenosis, and then selective angiography is performed to determine a stenosis site and blood vessel size information. The angiographic catheter is replaced with a guidewire (the guidewire is introduced and then withdrawn from the catheter). A balloon catheter pre-installed with the pulmonary artery stent of this embodiment is introduced into the stenosis site via the guidewire. By expanding the balloon catheter, the pre-installed pulmonary artery stent is expanded to a corresponding blood vessel size, ensuring that the pulmonary artery stent is completely expanded to fit the vessel wall, then the balloon pressure is released, the balloon catheter is finally withdrawn from the body, and the wound is stitched to complete the procedure. At a later stage, the growth of the blood vessel is observed through follow-up, and if the stent needs to be expanded to a larger size due to a large change in the blood vessel size, the procedure may be performed again to continue the expansion of the stent by introducing a balloon.

A fourth embodiment of the present disclosure provides a pulmonary artery stent, which further improves upon the structure of the metal stent of the pulmonary artery based on the first embodiment.

Figure 13:
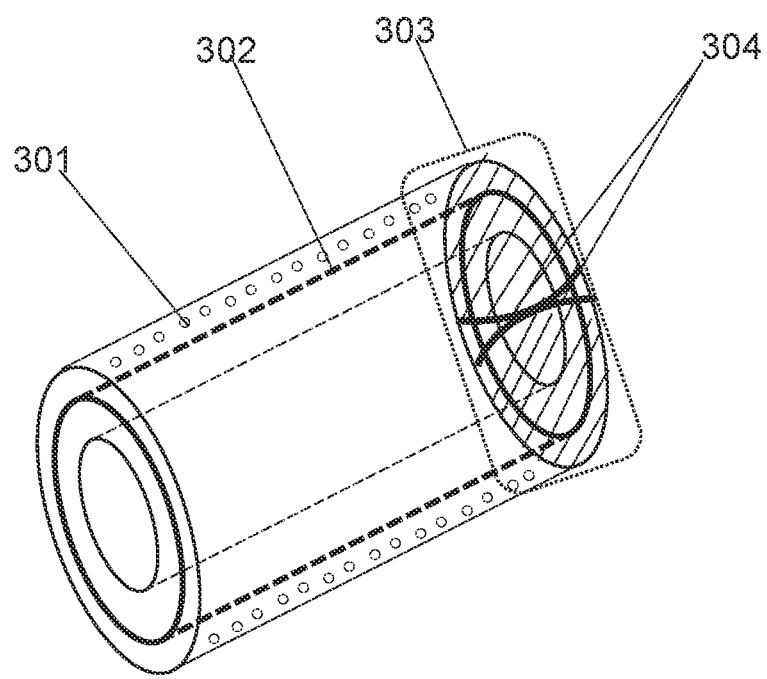
FIG. 13 is a schematic diagram illustrating an exemplary structure of another metal stent of the pulmonary artery stent according to some embodiments of the present disclosure.

FIG. 13 is a schematic diagram illustrating an exemplary structure of another metal stent of the pulmonary artery stent according to some embodiments of the present disclosure. In some embodiments, the metal stent of the pulmonary artery is a hollow tube, an inner cavity of the hollow tube is used to store biological drugs, and a wall of the hollow tube and an isolation membrane are provided with a corresponding micropore 301.

The hollow tube refers to a metal stent of a pulmonary artery that is provided with a hollow inner cavity between a wall of a blood flow channel and an outer wall of the metal stent in addition to a blood flow channel that allows blood flow to pass through. In some embodiments, the metal stent of the pulmonary artery is a hollow tube whose inner cavity may be used to store the biological drugs, and the biological drugs may include at least one of growth factor, BMP-2, thrombin, and insulin, etc. Types of the biological drugs are not limited herein.

In some embodiments, the biological drugs may slowly extravasate through the micropore 301 on the wall of the hollow tube and on the isolation membrane, and the size and shape of the micropore 301 may be adjusted depending on the size, pharmacology, and pharmacophore of the biological drugs in the inner cavity of the hollow tube. The size and shape of the micropore 301 may also be adjusted through an extravasation velocity of the biological drugs through the micropore 301 that needs to be controlled. In some embodiments, the micropore 301 may be either a nanopore or a micron pore, and the shape of the micropore 301 may be either a circular-like shape or a square shape. In some embodiments, the size and shape of the micropore 301 may also be designed according to actual needs or using a preset design, etc.

In some embodiments of the present disclosure, the biological drugs are stored through the inner cavity of the hollow tube and the extravasation velocity of the biological drugs is controlled by the size and shape of the micropore on the tube wall and isolation membrane, which allows the biological drugs to treat lesions caused by the pulmonary artery stent continuously for a long time while not relying on external therapeutic means.

In some embodiments, the inner cavity of the hollow tube is provided with a separation layer 302, which divides the inner cavity into at least two parts, and a separation membrane is disposed between an inner film and an outer film.

The separation layer 302 refers to a structure disposed in the inner cavity of the hollow tube and dividing the inner cavity of the hollow tube into two separate cavities therein. In some embodiments, the two separate cavities formed by separating the inner cavity of the hollow tube trough the separation layer 302 may be used to store the same or different biological drugs, respectively.

In some embodiments, a separate cavity close to the blood flow channel side may store biological drugs to treat lesions associated with the blood, and a separate cavity close to the vessel wall side may store biological drugs to treat lesions associated with the vessel wall. For example, the separate cavity close to the blood flow channel side may store a thrombolysis agent to treat thrombus, and the separate cavity close to the vessel wall side may store a tranexamic acid agent to inhibit cell proliferation.

In some embodiments, the separate cavity close to the blood flow channel side may be used in combination with a drug injection stent to treat the thrombus, such as drug injection of a larger or more thrombus present in a blood vessel at the pulmonary artery stent based on the drug injection stent for thrombolysis treatment. For more information about the drug injection stent, please refer to FIGS. 14-16 and their related descriptions.

In some embodiments, the two separate cavities formed by separating the inner cavity of the hollow tube through the separation layer 302 may also be used to store other drugs, for example, the separate cavity close to the blood flow channel side may store an anticoagulant or antiplatelet drug for treating the thrombus, and the separate cavity close to the vessel wall side may store an inflammatory factor inhibitor (e.g., adalimumab) for treating a vessel wall infection.

In some embodiments of the present disclosure, the inner cavity of the hollow tube is divided into two separate cavities by the separation layer 302, which allows for independent storage of biological drugs used to treat lesions associated with the vessel wall and lesions associated with the blood, thereby targeting the treatment of different types of lesions.

The separation membrane refers to a fibrous bundle structure disposed between the inner film and the outer film to enhance the durability, tensile strength, or circumferential expandability of the isolation membrane. In some embodiments, the separation membrane may also serve as a carrier for the biological drugs and treat the lesions with the surface coating and the biological drugs in the inner cavity of the hollow tube to maintain an adequate amount of the biological drugs for the pulmonary artery stent.

In some embodiments, the separation membrane may be a hydrogel with a three-dimensional reticulated polymer structure, and disposing the hydrogel between the inner film and the outer film may enhance the durability, tensile strength, or circumferential expandability of the isolation membrane, which avoids the need for multiple expansions of the pulmonary artery stent that may result in breakage of the isolation membrane.

In some embodiments, the hydrogel may be formed from a water-soluble polymer having a hydrophilic and similar structure to the soft tissues of the human body, so that it may lock in a large amount of water and better adapt to the blood vessel, reducing the lesions caused to the vessel wall. For example, the water-soluble polymer may be polyethylene glycol (PEG) or a natural macromolecular polysaccharide that mimics the intercellular matrix.

In some embodiments, the drug-loaded release of the separation membrane composed of the hydrogel depends on particle sizes of the biological drugs and sizes of the hydrogel meshes, so that the larger the drug-loaded particles and the denser the meshes are, the slower the drug dissolution is. In some embodiments, by controlling the covalent binding of the biological drugs (e.g., growth factors) in the hydrogel matrix, the release of the biological drugs may be slowed to treat lesions in the blood vessel consistently for a long time.

In some embodiments, the isolation membrane may further include a valve assembly that includes at least two barb-shaped valves, and the valve assembly is disposed on the inner film. The valve assembly is a member that may act as a one-way valve that only allows blood to flow in a correct direction to open. In some embodiments, barbs of the two valves face each other in opposite directions, and the barbs of the valve assembly point in the correct direction of blood flow.

In some embodiments of the present disclosure, the barb-shaped valve assembly is provided on the inner film so that it acts as the one-way valve that prevents backflow of blood in the blood channel of the pulmonary artery stent.

In some embodiments, as shown in FIG. 13, one end of the pulmonary artery metal stent includes a circumferential refill slot 303, the refill slot 303 is connected to the inner cavity of the hollow tube, the refill slot 303 includes a valve assembly 304 that may be topped off. A refill tube may be introduced into the refill slot during expansion or individual refill, and the refill tube includes a circumferential refill tip with an adjustable circumference, and the refill tip may be inserted into the refill slot 303 for refill. In some embodiments, the refill slot may serve as an object for a drug injection stent injecting drugs, at which point the drug injection stent may be viewed as the refill tube. For more information about the drug injection stent, please refer to FIGS. 14-16 and their related descriptions.

In some embodiments of the present disclosure, by providing the refill slot in the pulmonary artery metal stent, the refill tube is enabled to refill drugs to the inner cavity of the hollow tube in the body and maintain an adequate supply of biological drugs on the pulmonary artery stent.

In some embodiments, the pulmonary artery stent and the drug injection thrombolysis system may constitute a pulmonary artery vascular treatment device. In some embodiments, the drug injection thrombolysis system may include a delivery assembly, an external drug injection assembly, and a drug injection stent. The drug delivery assembly includes a sheath tube and a delivery handle. The sheath tube is fixedly connected to the delivery handle. The drug injection stent is stored at an inner end of the sheath tube; and the drug injection stent may include a drug delivery tube, a stent body capable of radical elastic expansion, and a thrombus filter. The stent body is fixed on the drug delivery tube, and the stent body may include a plurality of elastic tubes forming the stent structure. The elastic tubes are connected to the drug delivery tube, and a plurality of drug injection holes are provided on the elastic tubes. The thrombus filter is fixed on the drug delivery tube and located at a distal end of the stent body. The external drug injection assembly may include a drug injection connector and a syringe, the drug delivery tube of the drug injection stent is penetrated into the drug delivery assembly, an outer end of the drug delivery tube is connected to the drug injection connector, and the drug injection connector is connected to the syringe.

In some embodiments, the drug injection stent may be indicated for pulmonary artery thrombus removal treatment and may also be applied to thrombus removal treatment in blood vessels elsewhere in the body, and sites for thrombus removal treatment with the drug injection stent are not limited herein.

Figure 14:
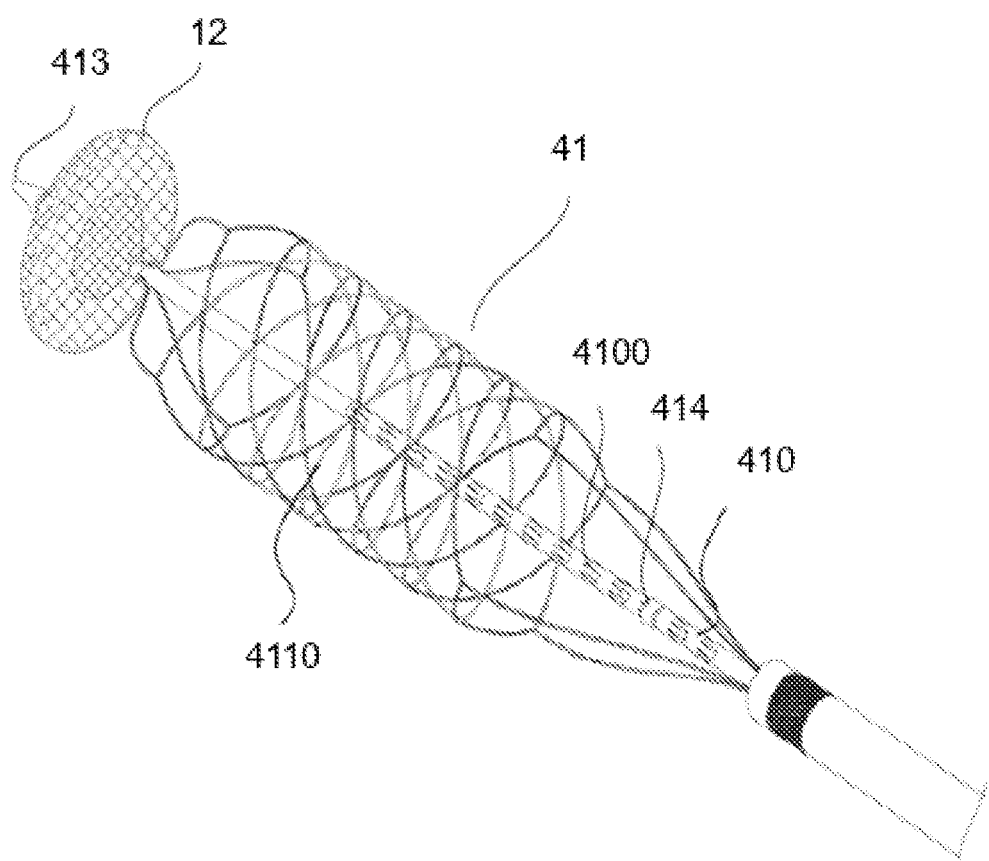
FIG. 14 is a schematic diagram illustrating a structure of a drug injection stent according to some embodiments of the present disclosure.
Figure 15:
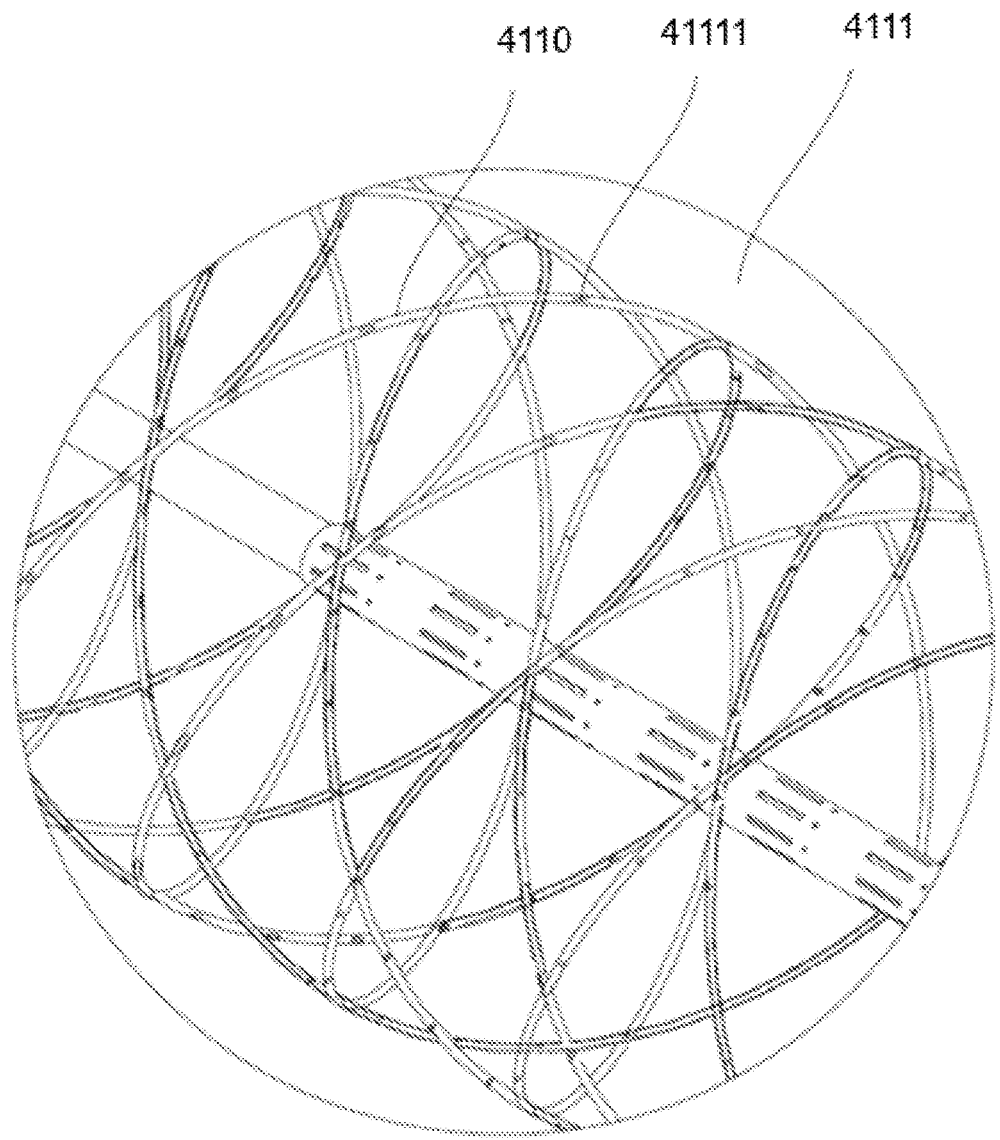
FIG. 15 is a schematic diagram illustrating a partially enlarged structure of a stent body of the drug injection stent according to some embodiments of the present disclosure.
Figure 16:
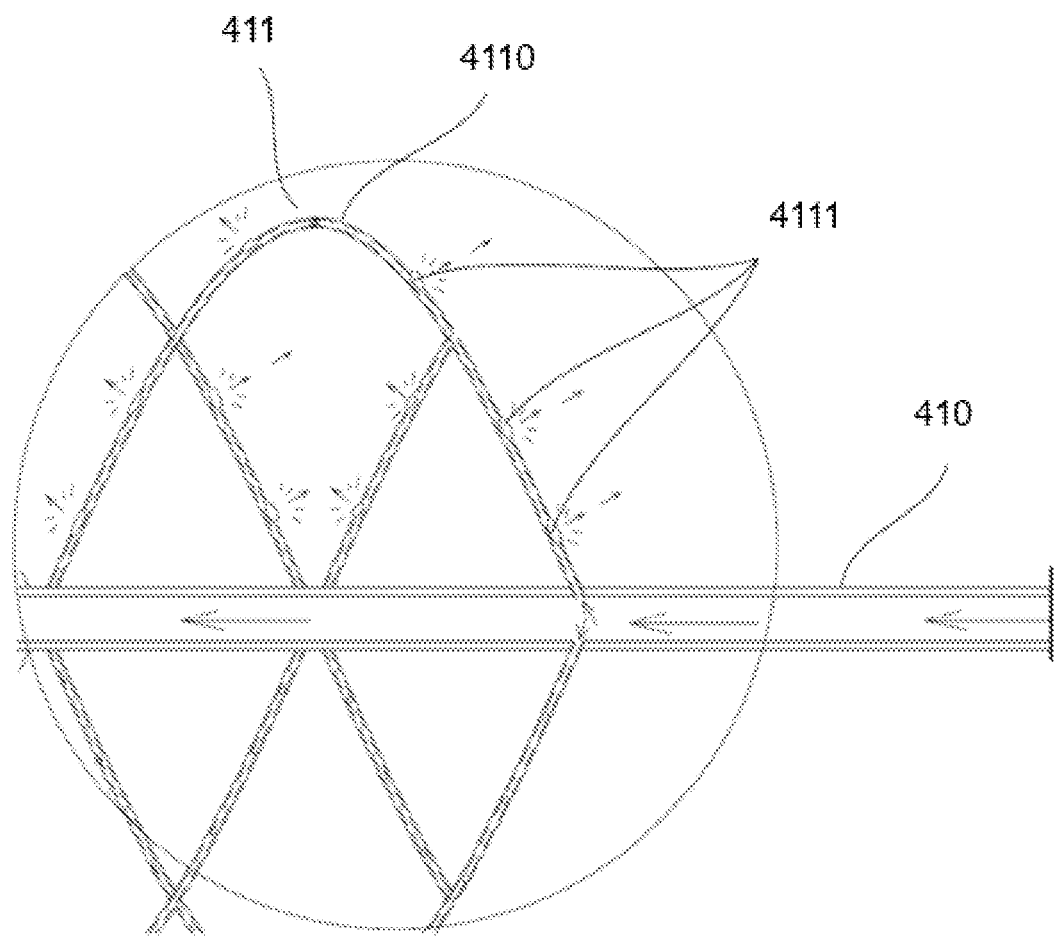
FIG. 16 is a schematic diagram illustrating a drug injection state of the drug injection stent according to some embodiments of the present disclosure.

As shown in FIGS. 14, 15, and 16, the drug injection stent 41 includes a drug delivery tube 410, a stent body 411 capable of radical elastic expansion, and a thrombus filter 412. The stent body 411 is fixed on the drug delivery tube 410, the stent body 411 includes a plurality of elastic tubes 4110 forming a stent structure. The elastic tubes 4110 are connected to the drug delivery tube 410, and a plurality of drug injection holes 4111 are provided on the elastic tubes 4110. The thrombus filter 412 is fixed on the drug delivery tube 410 and located at a distal end of the stent body 411.

In some embodiments, the drug injection stent 41 includes the stent body 411 provided on the drug delivery tube, the stent body 411 is formed into a stent structure by the plurality of elastic tubes 4110, the elastic tubes 4110 are provided with the drug injection holes 4111, and the elastic tubes 4110 are connected to the drug delivery tube 41. The inner end of the stent body 411 is also provided with a thrombus filter. In some embodiments, the drug injection stent 41 may be used in conjunction with the delivery assembly and the external drug injection assembly. Prior to use, the drug injection stent 41 may be stored in the sheath tube of the delivery assembly, and the drug delivery tube 410 may pass through the sheath tube 420 and the delivery handle 421, and be connected to the syringe 442 through the drug injection assembly. In the use, by operating the delivery handle 421, the drug injection stent 41 loaded in the sheath tube may be delivered to the position of the thrombus, and then the sheath tube is retracted to release the drug injection stent 41, and the drug injection stent 41 is embedded in the thrombus after self-expansion and opening, and the thrombolysis agent is injected through the syringe, and the thrombolysis agent reaches the elastic tubes of the drug injection stent 41 through the drug injection holes on the elastic tubes and is injected into the thrombus, so that the thrombolysis agent can act on the thrombus precisely and in a large area, thus improving the thrombolysis efficiency, and also helping to save the dosage of the agent and the treatment time, and the thrombus filter can effectively prevent small pieces of thrombus from escaping to the distal vessels.

In some embodiments, when a larger or more thrombus is present in a blood vessel with the pulmonary artery stent, the thrombolysis agent stored in the inner cavity of the hollow tube of the pulmonary artery stent alone may not completely perform thrombolysis on the thrombus, and the drug injection stent may be used in combination. The drug injection stent is made to expand and open into the thrombus of the blood vessel in which the pulmonary artery stent is placed, and the thrombolysis agent is injected into the thrombus via the syringe, causing the larger or more thrombus to turn into a smaller or lesser thrombus by preliminarily performing the thrombolysis. At this time, the thrombolysis agent in the inner cavity of the hollow tube of the pulmonary artery stent can be extravasated through the micropore 301 of the tube wall and act on the smaller or lesser thrombus to complete the thrombolysis.

In some embodiments, the drug injection stent may be a refill tube that refills a drug into the refill slot 303 on the pulmonary artery metal stent. In some embodiments, the drug injection stent may be used with the delivery assembly and the external drug injection assembly to refill the drug into the refill slot 303, and the drug injection stent is connected to the syringe via the drug delivery tube that passes through the sheath tube, delivery handle, and drug injection assembly, when the drug injection stent is used to refill the drug into the refill slot 303, the drug injection stent loaded in the sheath tube may be delivered to the refill slot 303 by operating the delivery handle to open the valve assembly 304 on the refill slot 303 and enter the refill slot 303, and then the drug (such as the thrombolysis agent, etc.) is injected through the syringe. The drug reaches the elastic tubes of the drug injection stent through the drug delivery tube and is injected into the refill slot 303 through the drug injection holes on the elastic tubes, so that the drug in the refill slot 303 enters the inner cavity of the hollow tube connected with the refill slot to achieve the purpose of drug refill.

In some embodiments, the adequacy of biological drugs on the pulmonary artery stent is maintained by providing the refill slot at one end of the hollow tube of the pulmonary artery metal stent, allowing the refill tube to refill the inner cavity of the hollow tube.

In some embodiments, the stent body 411 may be a stent unit and at least one end of each elastic tube 4110 of the stent body 411 is connected to the drug delivery tube 410. Specifically, as shown in FIG. 14, when expanded, a body portion of the stent unit is approximately cylindrical in shape, surrounds the drug delivery tube 410, and extends along the axial direction of the drug delivery tube 410. The stent unit may also be of other shapes suitable for processing and drug injection, which is not limited here.

In some embodiments, the stent body 411 may be made of an elastic metal tube or an elastic polymeric material tube. In some embodiments, the stent body 411 may also be prepared by 3D printing, which is not limited here. In some embodiments, openings at both ends of the elastic tube may be connected to the drug delivery tube, or only an opening at one end away from the thrombus filter of the elastic tube may be connected to the drug delivery tube. In this embodiment, as shown in FIG. 16, the openings at the ends of the elastic tube 110 may be directly connected to the inner cavity of the drug delivery tube 410. In some embodiments, the elastic tubes may be connected to the drug delivery tube in any other suitable manner, which will not be limited here.

Further, the elastic tubes 4110 extend spirally along the axial direction of the drug delivery tube 410, thereby facilitating not only the formation of a stable support structure, but also the rapid and smooth flow of the agent in the elastic tube.

In some embodiments, the stent body 411 may include: an elastic tube extending along the axial direction of the drug delivery tube 410 and an elastic tube surrounding the drug delivery tube 410, wherein the drug injection holes 4111 may be provided in the elastic tube extending along the axial direction, and portions of the elastic tube surrounding the drug delivery tube may not be provided with the drug injection holes.

In some embodiments, the drug injection holes are evenly distributed on the elastic tubes, wherein the drug injection holes at each open position may be single holes and/or double holes symmetrically distributed. For example, as shown in FIG. 16, the drug injection holes 4111 are evenly distributed at a plurality of positions on a single elastic tube 4110, and each position is provided with one drug injection hole 4111. In some embodiments, the distribution of the drug injection holes on the elastic tubes may also be in other forms (e.g., distributed at equidistant intervals), and the drug injection holes may also be holes in other porous distribution forms.

In some embodiments, two drug injection holes may also be distributed symmetrically at each open position of the elastic tubes 4110, or single and double drug injection holes may also be staggered on the elastic tubes. When the drug injection holes are single holes, all the drug injection holes may be distributed on the same side of the elastic tubes, or different drug injection holes may be distributed on different sides of the elastic tubes, which is not specifically limited herein.

In some embodiments, when two drug injection holes are symmetrically distributed at the same position on the elastic tubes 4110, the influence on uniformity of the drug injection due to the adhesion between the drug injection holes and the blood vessel wall at this position may be avoided. This embodiment is not limited to the specific structure of the stent body, as long as the thrombolysis agent can act on the thrombus in a large area.

Figure 17:
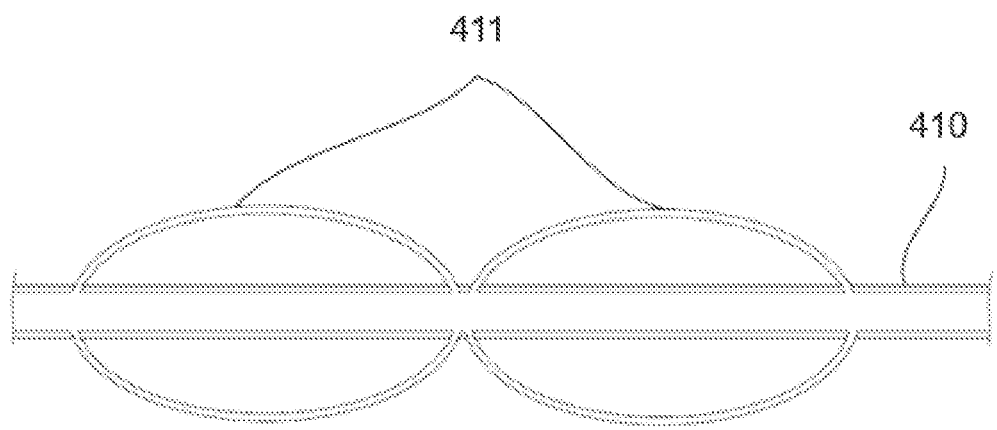
FIG. 17 is a schematic diagram illustrating a structure of the stent body according to some other embodiments of the present disclosure.
Figure 18:
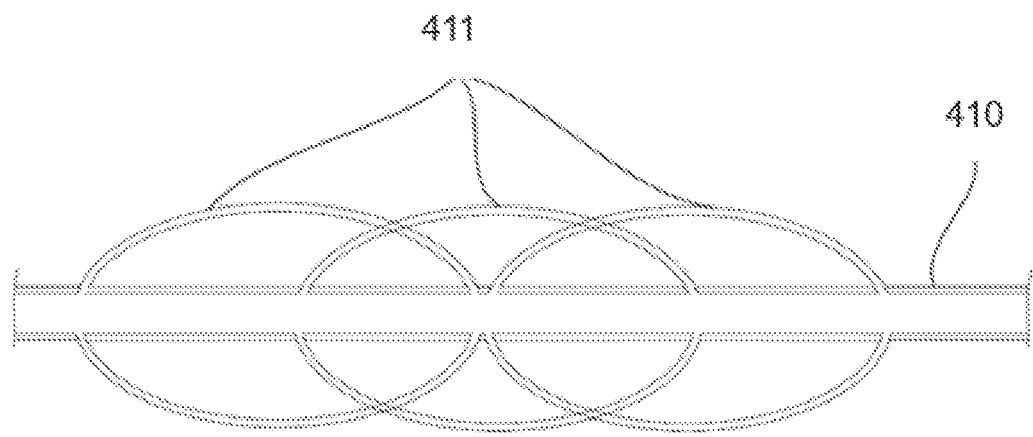
FIG. 18 is a schematic diagram illustrating a structure of the stent body according to some further embodiments of the present disclosure.

Based on the above embodiments, in some embodiments, the stent body 411 may further include a plurality of stent units, the plurality of stent units are provided axially aligned or axially staggered along the drug delivery tube 410. By way of example, as shown in FIG. 17, the stent body 411 may include two stent units, and the two stent units are provided aligned. As shown in FIG. 18, the stent body 411 may include three stent units, and the three stent units are axially staggered along the drug delivery tube. By providing the plurality of stent units, the flow path of the drug in the elastic tubes can be significantly shortened, which is conducive to improving the flow velocity of the drug in the drug injection stent.

Optionally, in some embodiments, the thrombus filter 412 is disc-shaped, and the thrombus filter 412 may be made of an elastic metal tube or a thin woven tube of medical polymeric material. The thrombus filter 412 may adapt to the shape and size of the blood vessel after self-expansion and opening, and the mesh of the thrombus filter 412 may be a finer diamond-shaped, near-rhombus-shaped mesh, so as to effectively filter and intercept the thrombus that escapes when the thrombolysis agent performs the thrombolysis on the thrombus. It should be understood that the embodiment does not limit the shape and size of the mesh of the thrombus filter.

In some embodiments, the drug injection stent 41 may also include a tip 413 provided at the inner end of the drug delivery tube 410.

In some embodiments, the drug delivery tube 410 is further provided with a side hole 4100 at a position of the stent body 411. The side hole 4100 is a through hole and is connected to the cavity of the drug delivery tube 410. The thrombolysis agent may be sprayed on a thrombus axis region through the side hole 4100 of the drug delivery tube 410.

In some embodiments, as shown in FIG. 14, the drug delivery tube 410 is further provided with a developing part 414 for indicating the position of the stent body at the position of the stent body. By way of example and not limitation, the developing part 414 may be an annular structure, thereby facilitating the determination of whether the stent body accurately reaches the position of the thrombus under an X-ray machine.

In some embodiments, the drug injection stent may be released at the position of the thrombus and then automatically expanded and adapted to the shape and size of the blood vessel, and the thrombolysis agent may be precisely injected into the thrombus through the drug injection holes of the stent body and the side hole of the drug delivery tube, etc., thus acting directly on the thrombus in a large area, allowing effective thrombolysis and clearance of the thrombus in a shorter time period using a smaller dose of the agent, thereby reducing the operation time and avoiding the risk of major bleeding.

Figure 20:
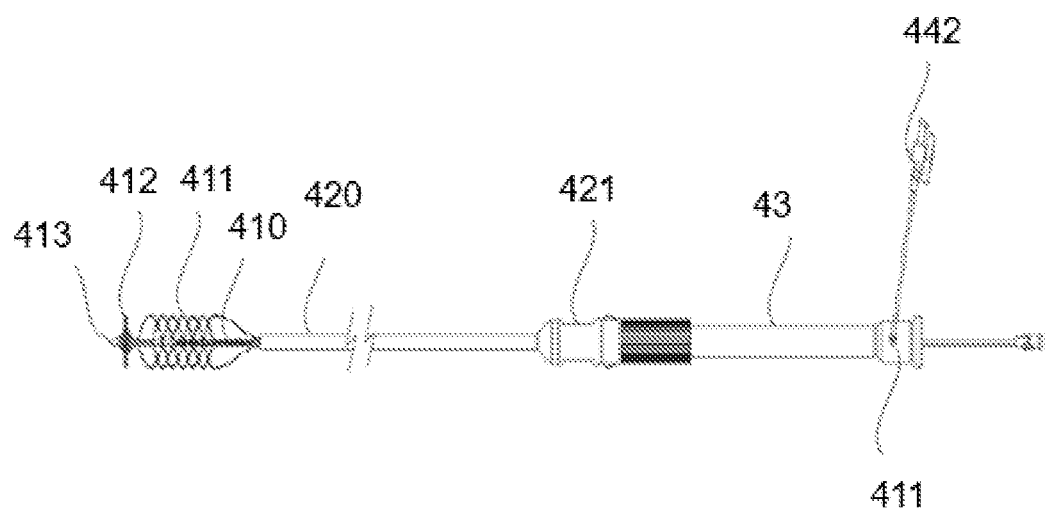
FIG. 20 is a schematic diagram illustrating a structure of the drug injection thrombolysis system according to some embodiments of the present disclosure.

This embodiment also provides a drug injection thrombolysis system that may be used for interventional thrombolysis treatment for pulmonary artery embolism to unblock pulmonary artery blood vessels to restore blood flow patency. As shown in FIG. 20, the system includes a delivery assembly, an external drug injection assembly, and the drug injection stent 41 as described in the preceding embodiment. The drug delivery assembly includes the sheath tube 420 and the delivery handle 421, the sheath tube 420 is fixedly connected to the delivery handle 421, the drug injection stent 41 is stored at the inner end of the sheath tube 420. The external drug injection assembly includes the drug injection connector 441 and the syringe 442. The drug delivery tube 410 of the drug delivery stent 41 is inserted into the delivery assembly, the outer end of the drug delivery tube 410 is connected to the drug delivery connector 441, and the drug delivery connector is connected to the syringe 442.

In some embodiments, the sheath tube 420 is threadedly connected to the delivery handle 421 and the sheath tube 420 is a sheath tube 421 capable of elastic retraction that has a larger caliber than a diameter of an inlet of the delivery handle when the sheath tube is naturally open. When loading the drug injection stent 41, the sheath tube 420 and the delivery handle 421 may be separated, and at this time, the sheath tube in a natural state has a larger caliber, which facilitates the loading of the drug injection stent 41. After the drug injection stent 41 is loaded, the sheath tube 420 is screwed into the delivery handle 421. Since the diameter of the inlet of the delivery handle 421 is smaller, the sheath tube becomes thinner as the length of the sheath tube screwed into the delivery handle 421 increases, and the caliber of the end storing the drug injection stent 41 of the sheath tube 420 is thinner accordingly.

Figure 19:
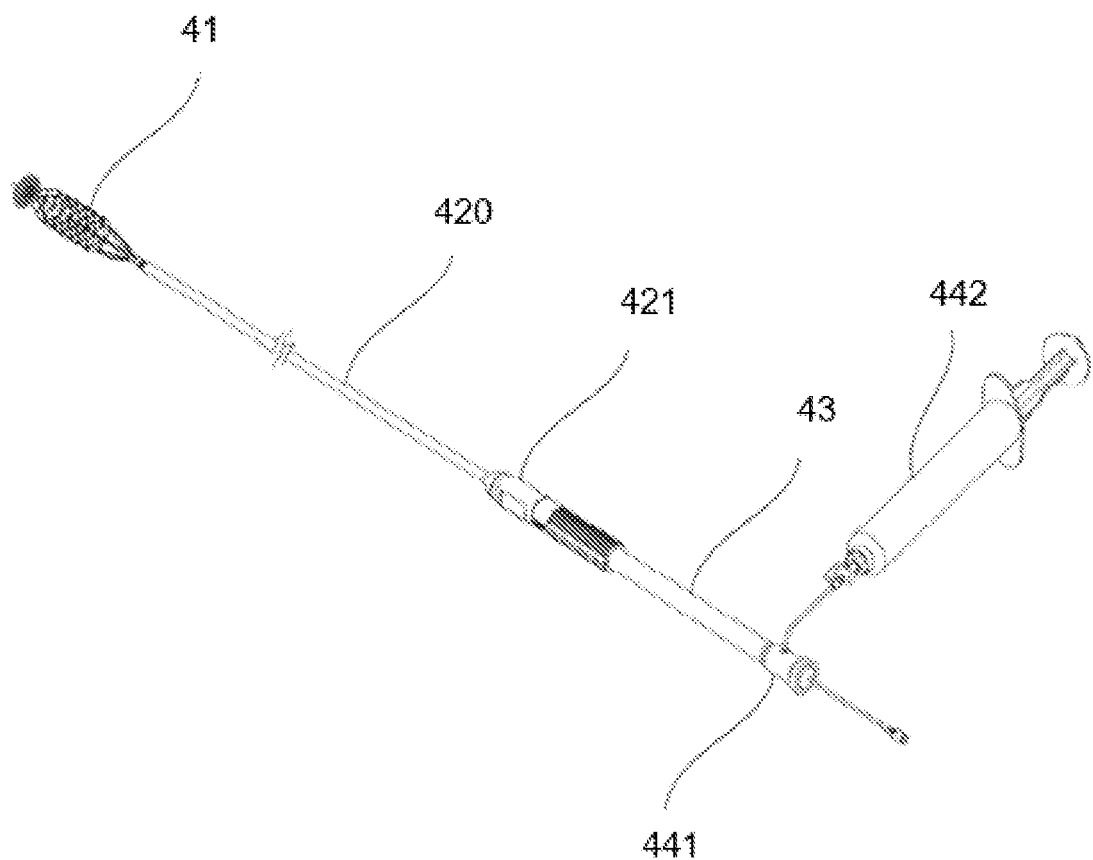
FIG. 19 is a schematic diagram illustrating a three-dimensional structure of a drug injection thrombolysis system according to some embodiments of the present disclosure.

In some embodiments, as shown in FIG. 19, the loading position of the drug injection stent 41 in the sheath tube 420 is a black tube segment at the inner end of the sheath tube. In use, the sheath tube 420 is driven by the delivery handle 421 to slide in an axial direction, and after the drug injection stent 41 reaches the position of the thrombus, then a portion of the sheath tube is rotated out from the delivery sheath tube 420. At this time, the caliber of the sheath tube 420 automatically becomes thicker, then the delivery handle 421 may be pulled back, and the sheath tube 420 may release the drug injection stent 41 therein after retreating with the delivery handle 421. This embodiment controls the thickness of the caliber of the sheath tube by the delivery handle, making it easier to load and release the drug injection stent 41. In some embodiments, the sheath tube 420 and the delivery handle

421 may be separately made into a split-piece structure, or the sheath tube 420 may be made together with the delivery handle 421 in a one-piece structure.

In some embodiments, the system may also include a recovery handle 43, the recovery handle 43 is slidingly connected to the delivery handle 421, the recovery handle 43 is fixedly connected to the drug injection connector 441, and the drug delivery tube 410 is penetrated into the recovery handle 43. The drug delivery tube 410 establishes a drug delivery channel with the syringe 442 through the drug injection connector 441. This embodiment does not limit the structure of the drug injection joint, any joint structure that may connect the drug delivery tube to the syringe 442 belongs to the scope of protection of the present disclosure.

In conjunction with the accompanying drawings, the manners and steps for using the drug injection thrombolysis system of this embodiment are as follows.

In minimally invasive interventional procedures for thrombus removal in pulmonary embolism, a device interventional channel is established in the femoral vein vessel through a puncture needle, guide wire, catheter, and puncture sheath. The catheter is introduced via an intravascular interventional channel technique to a central pulmonary artery, and then selective main pulmonary angiography is performed to determine a blood vessel site of the pulmonary artery thrombus. The angiographic catheter is replaced with a guidewire (the guidewire is introduced and then withdrawn from the catheter).

The sheath tube 420 loaded with the drug injection stent 41 of this embodiment is conveyed along the guidewire to the position of the pulmonary artery thrombus, and the position of the stent body 411 at the thrombus may be confirmed by the developing performance of the stent body and the developing part under the X-ray machine. The delivery handle 421 may be operated to adjust the position of the stent body 411 so that the stent body 411 may completely cover the thrombus.

After determining the position of the drug injection stent at the thrombus, the recovery handle 43 is held and the delivery handle 421 is retracted causing the drug injection stent 41 to be released and then expanded and extended. The thrombolysis agent is injected into the drug injection connector 441 by the syringe 442, and since the drug injection connector 441 is connected to the drug delivery tube and the drug injection stent 41, the thrombolysis agent reaching the drug injection stent 41 can be precisely injected and acted on the thrombus through the drug injection holes of the drug injection stent 41 and the side holes of the drug delivery tube. The thrombolysis agent can promote fibrinolysis and dissolve the thrombus. The thrombus may be dislodged during the thrombolysis process by the action of the blood flow and thrombolysis agent, and in this case, the thrombus filter may filter and intercept the thrombus, thus preventing the dislodged thrombus from escaping.

After the thrombolysis is complete, the drug injection stent 41 is retrieved into the sheath tube 420 along with the thrombus filter 412 by holding the delivery handle and pulling the retrieval handle, which is then withdrawn from the body.

In some embodiments of the present disclosure, the drug injection thrombolysis system may spray the thrombolysis agent precisely on the thrombus, thus acting directly on the thrombus in a large area, which allows effective thrombolysis and clearance of the thrombus in a shorter time period using a smaller dose of the agent, thereby reducing the procedure time and avoiding the risk of major bleeding.

Although only the method for using the drug injection stent with the syringe 442 is described herein, it should be understood that the drug injection stent disclosed in the embodiments may also be used with other suitable drug injection devices.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, numbers describing the number of ingredients and attributes are used. It should be understood that such numbers used for the description of the embodiments use the modifier "about", "approximately", or "substantially" in some examples. Unless otherwise stated, "about", "approximately", or "substantially" indicates that the number is allowed to vary by ±20%. Correspondingly, in some embodiments, the numerical parameters used in the description and claims are approximate values, and the approximate values may be changed according to the required characteristics of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

For each patent, patent application, patent application publication, or other materials cited in the present disclosure, such as articles, books, specifications, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure.

Finally, it should be understood that the embodiments described in the present disclosure are only used to illustrate the principles of the embodiments of the present disclosure. Other variations may also fall within the scope of the present disclosure. Therefore, as an example and not a limitation, alternative configurations of the embodiments of the present disclosure may be regarded as consistent with the teaching of the present disclosure. Accordingly, the embodiments of the present disclosure are not limited to the embodiments introduced and described in the present disclosure explicitly.

What is claimed is:

1. A drug injection thrombolysis system, comprising:
    a delivery assembly, an external drug injection assembly, and a drug injection stent, wherein
    the drug injection stent includes a drug delivery tube, a stent body capable of radical elastic expansion, and a thrombus filter, wherein
        the stent body is fixed on the drug delivery tube, the stent body includes a plurality of elastic tubes forming a stent structure, the plurality of elastic tubes are connected to the drug delivery tube, a plurality of drug injection holes are provided on the plurality of elastic tubes; and
        the thrombus filter is fixed on the drug delivery tube and located at a distal end of the stent body;
    the delivery assembly includes a sheath tube for storing the drug injection stent and a delivery handle connected to the sheath tube;
    the external drug injection assembly includes a drug injection connector, the drug delivery tube is penetrated into the delivery assembly, an outer end of the drug delivery tube is connected to the drug injection connector; and
    the sheath tube is threadedly connected to the delivery handle, the sheath tube is a sheath tube capable of elastic retraction, and the sheath tube has a caliber larger than a diameter of an inlet of the delivery handle when naturally opened.

2. The drug injection thrombolysis system of claim 1, further comprising: a recovery handle, wherein the recovery handle is slidingly connected to the delivery handle, the recovery handle is fixedly connected to the drug injection connector, and the drug delivery tube is penetrated into the recovery handle.

3. The drug injection thrombolysis system of claim 1, wherein
    the stent body is a stent unit, and at least one end of each elastic tube of the stent body is connected to the drug delivery tube; or
    the stent body includes a plurality of stent units, and the plurality of stent units are provided parallel or staggered along an axial direction of the drug delivery tube.

4. The drug injection thrombolysis system of claim 1, wherein the plurality of drug injection holes are evenly distributed on the plurality of elastic tubes, and the drug injection holes are single holes and/or symmetrically distributed double holes.

5. The drug injection thrombolysis system of claim 1, wherein a side hole is provided at a position of the stent body on the drug delivery tube.

6. The drug injection thrombolysis system of claim 1, wherein a developing part for indicating a position of the stent body is provided on the drug delivery tube.

7. The drug injection thrombolysis system of claim 1, wherein the plurality of elastic tubes extend spirally in an axial direction of the drug delivery tube.

8. The drug injection stent of claim 1, wherein the plurality of elastic tubes are made of elastic metal tubes or elastic polymer tubes.

9. A pulmonary artery vascular treatment device, comprising:
    a pulmonary artery stent, a drug injection stent, and a drug injection thrombolysis system, wherein
        the drug injection stent includes a drug delivery tube, a stent body capable of radical elastic expansion, and a thrombus filter, wherein
            the stent body is fixed on the drug delivery tube, the stent body includes a plurality of elastic tubes forming a stent structure, the plurality of elastic tubes are connected to the drug delivery tube, a plurality of drug injection holes are provided on the plurality of elastic tubes;
            the thrombus filter is fixed on the drug delivery tube and located at a distal end of the stent body; and
        the pulmonary artery stent includes a metal stent capable of circumferential expansion; and an isolation membrane wrapping the metal stent to isolate the metal stent from an external environment, and the isolation membrane having a circumferential tensile strength less than an axial tensile strength, wherein
            the metal stent includes a plurality of support segments, the support segments include a plurality of double wave segments arranged in a circumferential direction, two wave segments of the double wave segments are symmetrically arranged; and each of the double wave segments is composed of a plurality of end-to-end support ribs arranged in a wavy shape, support ribs located at connecting ends of the double wave segments and in close proximity to each other are used as connecting ribs, and connecting ribs of any two double wave segments adjacent to each other in the circumferential direction are cross-connected;
            the isolation membrane includes an inner film and a plurality of segments of a strip-shaped outer film, or the isolation membrane includes the inner film and a plurality of segments of cylinder-shaped outer film; the inner film covers an inner surface of the metal stent, and each segment of the outer film is connected to the inner film and covers each of the support segments, respectively; each of the support segments is connected by the isolation membrane; and a surface of the isolation membrane is coated with a surface coating containing a biological drug; and the drug injection thrombolysis system includes a delivery assembly and an external drug injection assembly, wherein the delivery assembly includes a sheath tube for storing the drug injection stent and a delivery handle connected to the sheath tube; and the external drug injection assembly includes a drug injection connector, the drug delivery tube is penetrated into the delivery assembly, an outer end of the drug delivery tube is connected to the drug injection connector.

10. The pulmonary artery vascular treatment device of claim 9, wherein the metal stent is a hollow tube, an inner cavity of the hollow tube is used to store the biological drug;
a wall of the hollow tube and the isolation membrane are provided with micropores; and
the inner cavity of the hollow tube is provided with a separation layer, the separation layer divides the inner cavity into at least two parts, and a separation membrane is disposed between the inner film and the outer film.

11. The pulmonary artery vascular treatment device of claim 10, wherein one end of the metal stent includes a circumferential refill slot, and the refill slot is connected to the inner cavity of the hollow tube; wherein
the refill slot includes a valve assembly capable of being pushed open.

12. The pulmonary artery vascular treatment device of claim 9, wherein the isolation membrane further includes a valve assembly, the valve assembly includes at least two barb-shaped valves, and the valve assembly is disposed on the inner film.

13. The pulmonary artery vascular treatment device of claim 9, wherein a three-dimensional reticulated fiber bundle structure is provided between the inner film and the outer film of the isolation membrane, and the three-dimensional reticulated fiber bundle structure is a carrier for the biological drug.

14. The pulmonary artery vascular treatment device of claim 9, wherein
the stent body is a stent unit, and at least one end of each elastic tube of the stent body is connected to the drug delivery tube; or
the stent body includes a plurality of stent units, and the plurality of stent units are provided parallel or staggered along an axial direction of the drug delivery tube.

15. The pulmonary artery vascular treatment device of claim 9, wherein the plurality of drug injection holes are evenly distributed on the plurality of elastic tubes, and the drug injection holes are single holes and/or symmetrically distributed double holes.

16. The pulmonary artery vascular treatment device of claim 9, wherein a side hole is provided at a position of the stent body on the drug delivery tube.

17. The pulmonary artery vascular treatment device of claim 9, wherein a developing part for indicating a position of the stent body is provided on the drug delivery tube.

18. The pulmonary artery vascular treatment device of claim 9, wherein the plurality of elastic tubes extend spirally in an axial direction of the drug delivery tube.

19. The pulmonary artery vascular treatment device of claim 9, wherein the plurality of elastic tubes are made of elastic metal tubes or elastic polymer tubes.

\* \* \* \* \*